(12) United States Patent
Hirohata et al.

(10) Patent No.: US 8,865,669 B2
(45) Date of Patent: Oct. 21, 2014

(54) DNA FRAGMENT AND USE THEREOF

(75) Inventors: Satoshi Hirohata, Okayama (JP); Yoshifumi Ninomiya, Okayama (JP); Shozo Kusachi, Okayama (JP); Faruk Hatipoglu Omer, Okayama (JP)

(73) Assignee: National University Corporation Okayama University, Okayama (JP)

( * ) Notice: Subject to any disclaimer, the term of this patent is extended or adjusted under 35 U.S.C. 154(b) by 120 days.

(21) Appl. No.: 12/865,996

(22) PCT Filed: Feb. 4, 2009

(86) PCT No.: PCT/JP2009/051907
§ 371 (c)(1),
(2), (4) Date: Aug. 3, 2010

(87) PCT Pub. No.: WO2009/099112
PCT Pub. Date: Aug. 13, 2009

(65) Prior Publication Data
US 2011/0023155 A1 Jan. 27, 2011

(30) Foreign Application Priority Data
Feb. 4, 2008 (JP) .................................. 2008-024071

(51) Int. Cl.
| | | |
|---|---|---|
| A01N 43/04 | (2006.01) |
| C12N 15/00 | (2006.01) |
| C07H 21/02 | (2006.01) |
| C07H 21/04 | (2006.01) |
| C12N 15/85 | (2006.01) |
| C12N 9/64 | (2006.01) |
| A61K 48/00 | (2006.01) |

(52) U.S. Cl.
CPC ............ *C12N 15/85* (2013.01); *C12N 2830/00* (2013.01); *A61K 48/0058* (2013.01); *C12N 9/6489* (2013.01); *C12N 2830/002* (2013.01); *G01N 2800/324* (2013.01)
USPC ................... 514/44 R; 435/320.1; 536/23.1; 536/24.1

(58) Field of Classification Search
CPC ............... C12N 15/85; C12N 2830/00; C12N 2830/002; A61K 48/0058; G01N 2800/324
USPC ............. 514/44 R; 435/320.1; 536/23.1, 24.1
See application file for complete search history.

(56) References Cited

FOREIGN PATENT DOCUMENTS

JP 2005-095173 A 4/2005
WO WO 2008/102002 A2 8/2008

OTHER PUBLICATIONS

Cargill et al., 2004, Geneseq Accession No. AFT27435, computer printout, p. 18-21.*
Gorecki, D., 2001, Expert Opin. Emerging Drugs, 6(2): 187-198.*
Lei et al., 2004, Basic Res Cardiol, vol. 99, p. 121-132.*
Yla-Herttuala et al., 2000, Lancet, vol. 355, p. 213-222.*
Thomas et al., 2003, Nature Reviews/ Genetics, vol. 4, p. 346-358.*
Lebedeva et al., 2003, Seminars in Cancer Biology, vol. 12, p. 169-178.*
Skolnick et al., 2000, Trends in Biotech, vol. 18, p. 34-39.*
Tomasinsig et al., 2005, Current Protein and Peptide Science, vol. 6, p. 23-34.*
Smallwood et al., 2002 Virology, vol. 304, p. 135-145.*
Chattopadhyay et al., 2004, Virus Research, vol. 99, p. 139-145.*
Kodama et al., 2006, Current Medicinal Chemistry, vol. 13, p. 2155-2161.*
Takahashi et al., 2012, Frontiers in Bioscience, vol. S4, p. 133-141.*
Kaur et al., 2009, Current Gene Therapy, vol. 9. p. 434-458.*
European Patent Office, Supplementary European Search Report for European Patent Application No. 09 70 8976 (Jun. 24, 2011).
Nakamura et al., *Circulation Journal*, 68(Suppl. 1): 110, Item FRS-078 (2004).
Nakamura et al., *J. Biochem.*, 136: 439-446 (2004).
Shibata et al., *Gene Therapy*, 7: 493-498 (2000).
Vazquez et al., *The Journal of Biological Chemistry*, 274(33): 23349-23357 (1999).
Vazquez et al., Database GenBank [online], Accession No. AF060152, retrieved on Feb. 17, 2009 from URL http://www.ncbi.nlm.nih.gov/entrez/viewer.fcgi?5725505:NCBI:11737362.
Cilek et al., *Cell Biology International*, 35(1): 1-8 (2011), which is submitted herewith in the form of Accepted Manuscript CBI20100290, The Authors Journal compilation, Portland Press Limited (Aug. 26, 2010).
Doyle et al., *Molecular Endocrinology*, 18(10): 2463-2478 (2004).
*The Japanese Society for Connective Tissue*, 34(1): 87 (2002), Concise Statement of Relevance.

* cited by examiner

*Primary Examiner* — Shin Lin Chen
(74) *Attorney, Agent, or Firm* — Leydig, Voit & Mayer, Ltd.

(57) ABSTRACT

The invention relates to a DNA consisting of the nucleotide sequence shown in SEQ ID NO: 1, or a nucleotide sequence the same or substantially the same as a partial nucleotide sequence thereof containing at least one HRE consensus sequence, which transiently has a transcription promoting activity in a vascular endothelial cell-specific manner in a hypoxic state, or a vector containing a promoter containing the DNA, and the like. The prophylaxis and/or treatment, as well as diagnosis, of acute ischemic diseases are enabled by connecting a prophylactic and/or therapeutic gene or a reporter gene to the downstream of the vector and administering same to mammals.

17 Claims, 8 Drawing Sheets

FIG. 2
(A)
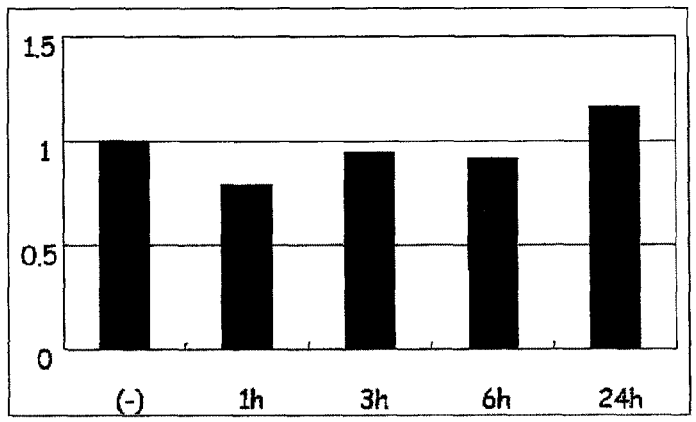
(B)
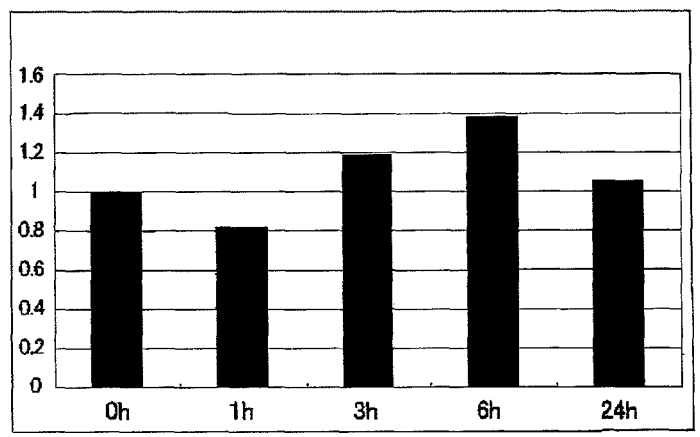
(C)
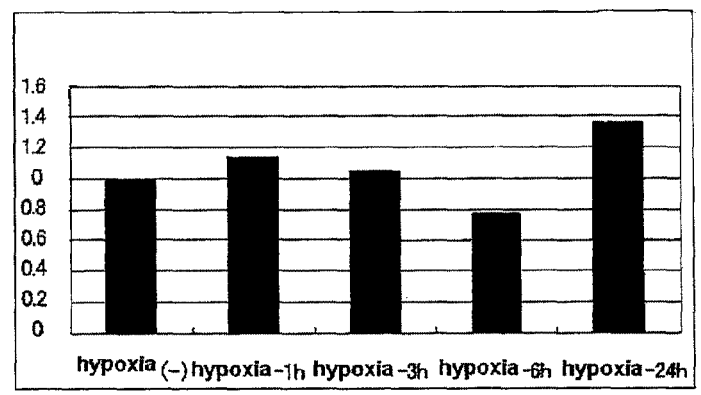

FIG. 5

```
actaagccct tcagaagtaa gctgagttgc ttctctctgc cattcttgct catttgattt      60
ttcctgatga gtggaaagca atgtttttgt ttttgttttt caagtaagca atctcgctag     120
gaaaaaagaa gttggaaagc atccggaaaa gaaagcttgt aagagggacg tgtgggagaa     180
ctagaaggga cgcttctggc tggggccaac tgaagtgggg aagatctggg gaggagcgag     240
gaaaggaccc agatctactt ggagccaacc aagagaccgg acgggagtgg ggcggaaagg     300
cggagaccag ttcgagcact aacgcggggg cgcgcgagtg tgagggttgc gggtccgccc     360
ggggctaggg cggtcgctct cgccattgtc cccgcggctt tccgcctgtg aaacacgtcc     420
ttcctctggg tccttgagcc cctcccactt tttggagaga agagccactc agttttttttt    480
cctaaggacc tgttggtgga cctctcctcg ctttcgtaac gcggatatag ccttttccct     540
tcctggtagg aagaggaagg aggggtccgg gaaggaagcc gatttccttc tttccccctc     600
tgcacgcttg ctagcccag cgatcgctgc tggcccccgg gtaggaaagt ggggttcctg      660
gccgtttctg cgacgctggc ctagggcttg cagctgctgt tgagtgaaag cacgcagact     720
ggcgggagcc gatcatttct cgaatgaaga agaaaaagcg caattccctc cttatgctct     780
agggaattga gccgcgtccc agatcaccca ttccagaaat gtgaaaccgg gccctcacaa     840
agtcgtctct ggtgaagagg tggcgtgcgg ggtgggggtt ggtggagggt gaaggcataa     900
gcaaacatat tttaaaatcc agatcgtagg aagtgtcacc tggcccctca cccaggcatg     960
ctttctgggg gaagcgcagg gccaagcttt ccctagaaaa gctggggcga agagagagca    1020
ggcggcggct aaggagctcc tggcaggctg ggaaggtgga gaagtggggt gaggtatttt    1080
tctagaaagt gtagccctag ctcatctcct agattgggga agagggaact gagggaggag    1140
ggaaggagac ccagggcagc tccaggatag ggaaatgttg aagaagggac tgcgttctcc    1200
aaccgaaccc tccctcctgg gaaccgcagc ccagcgcggt aactgagtta ccgcaaccgg    1260
gcggtgggga ggaagggtgg tccaggaaac cggcgaggga gaaaagcggt ggaagggaga    1320
gtcttctccc tggagcggcc ccagcagtac aaagtgctgg tcacagcgcc ccttccgccc    1380
ctagattgac gagcagtggc gtggagccag cgcggaggct gcccctccc cctcccgagc     1440
ccgcagcgcg gagcgcggtt tagcaccaac ggagccgggg gcggcgtctt tgggatggaa    1500
aagggccaaa ggggaggagt ggggtggggg tggggttttc actggtccac TATAaaagga    1560
ccgctcggct gcccggttct tgcactcgct ggaaagcggc tccgagccag gggctattgc    1620
aaagccaggg tgcgctaccg gacggagagg ggagagccct gagcagagtg agcaacatcg    1680
cagccaaggc ggaggccgaa gaggggcgcc aggcaccaat ctccgcgttg cctcagcccc    1740
ggaggcgccc cagagcgctt cttgtcccag cagagccact ctgcctgcgc ctgcctctca    1800
gtgtctccaa cttttgcgctg gaagaaaaac ttcccgcgcg ccggcagaac tgcagcgcct    1860
ccttttagtg actccgggag cttcggctgt agccggctct gcgcgccctt ccaacgaata    1920
atagaaattg ttaattttaa caatccagag caggccaacg aggctttgct ctcccgaccc    1980
gaactaaagg tccctcgctc cgtgcgctgc tacgagcggt gtctcctggg gctccaatgC    2040
AGCGAGCTGT GCCCGAGGGG TTCGGAAGGC GCAAGCTGGG CAGCGACATG GGAACGCGG     2100
AGCGGGCTCC GGGGTCTCGG AGCTTTGGGC CCGTACCCAC GCTGCTGCTG CTCGCCGCGG    2160
CGCTACTGGC CGTGTCGGAC G                                              2181
```

DNA FRAGMENT AND USE THEREOF

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 3,716 bytes ASCII (Text) file named "706784SequenceListing.txt," created Aug. 3, 2010.

TECHNICAL FIELD

The present invention relates to a DNA fragment capable of transiently promoting gene transcription in a vascular endothelial cell-specific manner in a hypoxic state, particularly an acute ischemic stage, and use thereof. More particularly, the present invention relates to a DNA containing a particular region of an ADAMTS1 gene promoter, a vector containing the DNA, as well as prophylaxis and/or treatment of a disease associated with a hypoxic state of vascular endothelial cells using the vector, detection of vascular endothelial cells in a hypoxic state and the like.

BACKGROUND ART

Accurate diagnosis and rapid treatment of acute ischemia is extremely important for acute ischemic diseases such as myocardial infarction and cerebral infarction, for which an effective treatment method is not present during the acute stage.

It is known that an extracellular matrix (ECM) plays an important role in the curing process after acute myocardial infarction. Since ECM molecules drastically change between accumulation and decomposition, cardiac muscle is remodeled after myocardial infarction, and it has been reported that a wide variety of biological substances such as protease, its inhibitor, growth factor and the like are involved in the ECM reconstitution. It is known that, in this process, expression of matrix metalloprotease (MMP) is particularly promoted and activated.

In addition, since cardiac muscle remodeling after myocardial infarction is also influenced by the formation and development (angiogenesis) of collateral vessels, the role of angiogenesis growth factor in acute myocardial infarction is also drawing attention. The vascular endothelial growth factor (VEGF) is a vascular endothelial mitogen considered to be involved in angiogenesis. VEGF shows promoted expression within 1 hr from ligation of the coronary artery. In addition, erythropoietin is a hormone enhancing growth of red blood cells, and promotes expression in a hypoxic state.

However, the expression of VEGF and erythropoietin is not induced in a particular organ or organum, and shows time dependency exhibiting increased expression as the ischemic interval grows longer. Thus, it was difficult to determine hypoxic state of a particular tissue by using them as biomarkers, and identification of the cause of transient acute ischemic state (e.g., acute ischemic disease) was also difficult.

ADAMTS (A Disintegrin And Metalloprotease with Thrombospondin motifs) is an MMP found in recent years. While expression of ADAMTS is not observed in normal tissues, it is induced by LPS stimulation, and recognizes a wide range of various substrates than MMP.

In addition, ADAMTS has been reported to not only decompose ECM but also function as an angiogenesis inhibitor. For example, ADAMTS-1 and ADAMTS-8 have been reported to have an antiangiogenesis action (see non-patent document 1), and ADAMTS-1 has been reported to suppress angiogenesis induced by FGF-2 and inhibit angiogenesis induced by VEGF. Furthermore, it is also known that ADAMTS-1 is bound to VEGF and inhibits phosphorylation of its receptor, VEGFR2 (see non-patent document 1).

Based on these findings, the present inventors have made a hypothesis that ADAMTS is involved in acute myocardial infarction, and found in rat myocardial infarction model that ADAMTS-1 is mainly hyperexpressed in vascular endothelial cells and cardiac muscle cells in the area of myocardial infarction and peripheral area thereof (see non-patent documents 2 and 3).

non-patent document 1: J. Biol. Chem., 1999 Aug. 13; 274 (33): 23349-23357
non-patent document 2: Connective Tissue, 34, 87 (2002)
non-patent document 3: J. Biochem. 136, 439-446 (2004)

DISCLOSURE OF THE INVENTION

Problems to be Solved by the Invention

An object of the present invention is to provide a means of detecting, in the initial stages of onset, acute ischemic diseases such as myocardial infarction and the like, for which an early diagnosis greatly influences the treatment or prognosis of thereof. In addition, it is to provide a drug delivery system capable of efficient delivery of a medicament to the lesion area of the disease, using which to provide a novel and effective prophylactic and/or therapeutic means for acute ischemic diseases.

Means of Solving the Problems

The present inventors have conducted intensive studies in an attempt to solve the above-mentioned problems and found that ADAMTS-1 protein is secreted in a vascular endothelial cell-specific manner in the initial stages of acute ischemia. Thus, they have verified whether a sequence capable of specifically promoting expression of gene in a hypoxic state is present in the promoter region of ADAMTS-1. As a result, they have clarified that a plurality of consensus sequences of a hypoxia response element (hereinafter sometimes to be referred to as HRE) commonly present in the transcription regulatory regions of genes such as erythropoietin, VEGF and the like induced in a hypoxic state are also present in the promoter region of ADAMTS-1. Moreover, they have found that a particular region containing HRE transiently promotes gene transcription in a hypoxic state and in a vascular endothelial cell-specific manner.

The present inventors have conducted further studies based on these findings and completed the present invention.

Accordingly, the present invention provides the following.
[1] An isolated DNA of any of the following (a) to (d):
(a) a DNA consisting of the nucleotide sequence shown in SEQ ID NO: 1
(b) a partial DNA of the DNA of the above-mentioned (a), which comprises at least one of the hypoxic state response elements consisting of respective nucleotide sequences shown by nucleotides 167-174, 284-291, 414-422, 427-434, 487-494, 862-869, 1034-1041 and 1398-1405, and shows a transient transcription promoting activity in a vascular endothelial cell-specific manner in a hypoxic state
(c) a non-human mammal ortholog of the DNA of the above-mentioned (a) or (b)
(d) a DNA consisting of a nucleotide sequence having a homology of not less than 80% to the DNA of any of the above-mentioned (a) to (c), and showing a transient transcription promoting activity in a vascular endothelial cell-specific manner in a hypoxic state.

[2] The DNA of any of the following (a) to (c):
(a) a DNA comprising nucleotides 527-1346 of SEQ ID NO: 1, which is a partial nucleotide sequence of the nucleotide sequence shown by SEQ ID NO: 1
(b) anon-human mammal ortholog of the DNA of the above-mentioned (a)
(c) a DNA consisting of a nucleotide sequence having a homology of not less than 80% to the DNA of the above-mentioned (a) or (b), and showing a transient transcription promoting activity in a vascular endothelial cell-specific manner in a hypoxic state.

[3] An expression vector comprising a promoter containing the DNA of [1] or [2], which transiently expresses a gene operably linked to the promoter in a hypoxic state in a vascular endothelial cell-specific manner.

[4] The vector of [3], wherein the transient expression in a hypoxic state occurs in an acute ischemic stage.

[5] The vector of [3] or [4], further comprising a prophylactic and/or therapeutic gene operably linked to the aforementioned promoter.

[6] A drug delivery system comprising the vector of [5], which can selectively deliver a product of a prophylactic and/or therapeutic gene to a vascular endothelial cell in a hypoxic state.

[7] A prophylactic and/or therapeutic agent for a disease associated with a vascular endothelial cell in a hypoxic state, which comprises the vector of [5].

[8] The agent of [7], wherein the disease is an acute ischemic disease.

[9] The vector of [3] or [4], further comprising a reporter gene operably linked to the aforementioned promoter.

[10] A reagent for detection of a vascular endothelial cell in a hypoxic state, comprising the vector of [9].

[11] The reagent of [10], which is for the diagnosis of an acute ischemic disease.

[12] A transgenic non-human animal harboring the vector of [9].

[13] A method for the prophylaxis and/or treatment of a disease associated with a vascular endothelial cell in a hypoxic state, which comprises using the vector of [5].

[14] The vector of [5] for the prophylaxis and/or treatment of a disease associated with a vascular endothelial cell in a hypoxic state.

[15] Use of the vector of [5] for the production of a prophylactic and/or therapeutic agent for a disease associated with a vascular endothelial cell in a hypoxic state.

Effect of the Invention

The DNA of the present invention can transiently promote gene transcription in a vascular endothelial cell-specific manner in a hypoxic state, particularly an acute ischemic stage, and therefore, the vector of the present invention comprising a promoter comprising the DNA can transiently express a desired gene in a vascular endothelial cell in a hypoxic state. In other words, it can selectively deliver a medicament, which is a gene product (protein, RNA), to a vascular endothelial cell in a hypoxic state.

In addition, a vector having a reporter gene connected to the downstream of the promoter can be used for detecting a vascular endothelial cell in a hypoxic state, and enables diagnosis of a disease associated with a vascular endothelial cell in a hypoxic state such as an acute ischemic disease and the like.

Moreover, a transgenic non-human animal containing a vector having a reporter gene connected to the downstream of the promoter can be used as an animal material for preparing an animal model of hypoxic state or acute ischemic disease, since it can easily visualize a hypoxic site.

BRIEF DESCRIPTION OF THE DRAWINGS

FIG. 2 shows expression of ADAMTS-1 in a cell other than endothelial cell in a low oxygen state: (A) human retinal pigment epithelial cell (ARPE); (B) human fibroblast; (C) human cardiac muscle cell (H9C2).

FIG. 3-1 shows expression of ADAMTS-1 in various cells in a low oxygen state: human umbilical vein endothelial cell (HUVEC); monkey kidney cell (COS7); human smooth muscle cell (SMC) from the left.

FIG. 3-2 shows expression of ADAMTS-1 in various cells in a low oxygen state: human umbilical vein endothelial cell (HUVEC); human fibroblast; monkey kidney cell (COS7); human retinal pigment epithelial cell (ARPE) from the left.

FIG. 5 shows nucleotide sequences of a promoter region, 5'UTR and a part of the coding region, of human ADAMTS-1 gene. The sequences in boxes show a part of HRE consensus sequences. TATA and ATG in bold capital letters show TATA sequence and initiation codon, respectively. Small letters show a promoter region (corresponding to SEQ ID NO: 1), and capital letters show a transcription region.

BEST MODE FOR CARRYING OUT THE INVENTION

Figure 1:
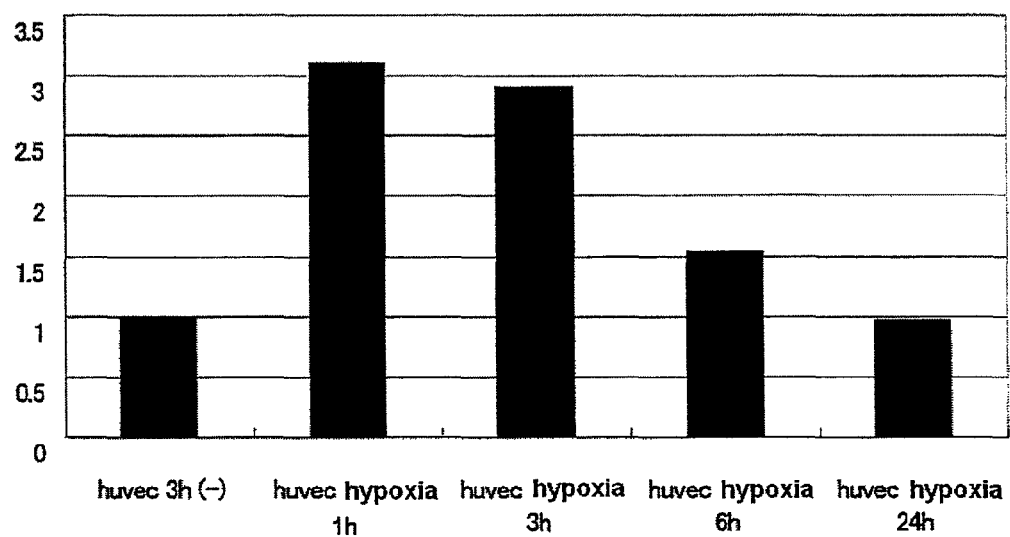
FIG. 1 shows expression of ADAMTS-1 in a human umbilical vein endothelial cell (HUVEC) in a low oxygen state.

The present invention provides a novel DNA capable of transiently promoting transcription of a gene at the downstream in a vascular endothelial cell-specific manner in a hypoxic state (hereinafter to be also referred to as "the DNA of the present invention"). Here, the "hypoxic state" is a condition where an oxygen partial pressure is lower than normal oxygen partial pressure in physiological conditions of vascular endothelial cells, which is particularly a condition causing an acute increase in the HIF-1 and/or HIF-2 expressions. While the normal oxygen partial pressure is vastly different depending on each organ in the body, the oxygen partial pressure causing a low oxygen gene response such as HIF-1 and the like is, for example, not more than 40 mmHg. A representative example of the hypoxic state developed in an animal individual is ischemia. Moreover, in a cell or tissue under culture, it refers to a condition showing an oxygen concentration of 1-5%.

The "transiently" refers to a given period in the duration of a hypoxic state, which is preferably an initial stage of a hypoxic state. Though subject to change depending on the kind of the vascular endothelial cells, it is, for example, immediately after the start of a hypoxic state to about 12 hr later, preferably about 1-6 hr later, for human umbilical vein endothelial cells (HUVEC) and the like, and, for example, a period of about 1-3 days for human coronary endothelial cell (HCAEC) and the like. The hypoxic state developed in an animal individual is a period corresponding to acute ischemia.

The DNA of the present invention is a DNA having a part (2039 nucleotides upstream from immediately before transcription start point) of human ADAMTS-1 promoter which is the nucleotide sequence shown in SEQ ID NO: 1, or the same or substantially the same nucleotide sequence with the partial DNA containing at least one HRE consensus sequence, which has a transient transcription promoting activity in a vascular endothelial cell-specific manner in a hypoxic state. Here, the "HRE consensus sequence" is a highly preserved sequence to which a hypoxia-inducible transcription factor (HIF)-1 and/or HIF-2 can be bound, and is a nucleotide sequence comprising "BACGTSSK wherein A is adenine, B is G (guanine), C (cytosine) or T (thymine), S is G or C, and K is G or T", or the nucleotide sequence wherein 1 to 3, preferably 1 or 2, bases are substituted, deleted, added or inserted, to which HIF-1 and/or HIF-2 can be bound. The binding potential of HIF-1 and HIF-2 to a mutant HRE sequence can be easily evaluated by a known gel shift assay and the like.

While HIF-1 and HIF-2 have two subunits of α and β, respectively, they are not particularly limited in the present specification. HRE consensus sequence may be a sequence capable of binding to either one of the subunits or to a complex consisting of the both subunits.

Examples of the HRE consensus sequence in the nucleotide sequence shown in SEQ ID NO: 1 include respective nucleotide sequences consisting of nucleotides 167-174, 284-291, 414-422, 427-434, 487-494, 862-869, 1034-1041 and 1398-1405. Therefore, any DNA can also be encompassed in the DNA of the present invention as long as it contains at least one of these nucleotide sequences, and shows a transient transcription promoting activity in a vascular endothelial cell-specific manner in a hypoxic state.

Preferably, the DNA of the present invention is a partial nucleotide sequence of the nucleotide sequence shown in SEQ ID NO: 1, contains the same or substantially the same nucleotide sequence consisting of nucleotides 527-1346 of SEQ ID NO: 1, and shows a transient transcription promoting activity in a vascular endothelial cell-specific manner in a hypoxic state.

Examples of the "substantially the same nucleotide sequence" include the nucleotide sequence shown in SEQ ID NO: 1 or a partial nucleotide sequence thereof, wherein 1) a nucleotide sequence wherein 1 or more bases (preferably 1-50 bases, more preferably 1-10 bases, further preferably 1-5, 4, 3 or 2 bases) are substituted by other bases, 2) a nucleotide sequence wherein 1 or more bases (preferably 1-50 bases, more preferably 1-10 bases, further preferably 1-5, 4, 3 or 2 bases) are deleted, 3) a nucleotide sequence wherein 1 or more bases (preferably 1-50 bases, more preferably 1-10 bases, further preferably 1-5, 4, 3 or 2 bases) are inserted, 4) a nucleotide sequence wherein 1 or more bases (preferably 1-50 bases, more preferably 1-10 bases, further preferably 1-5, 4, 3 or 2 bases) are added and 5) a nucleotide sequence comprising a combination of these, which have a transient transcription promoting activity in a vascular endothelial cell-specific manner during a hypoxic state. The transcription promoting activity can be evaluated by a binding assay with HIF-1 or HIF-2, or by measuring the expression under a hypoxic state of a reporter gene (e.g., luciferase, Green Fluorescent Protein (GFP) etc.) under control of a promoter containing a nucleotide sequence to be examined. The above-mentioned substitution, deletion, insertion and addition are desirably performed using a part other than the HRE consensus sequence.

Alternatively, as the "substantially the same nucleotide sequence", DNA capable of hybridizing with DNA consisting of a complementary nucleotide sequence with the nucleotide sequence shown in SEQ ID NO: 1 under stringent conditions, which has a transient transcription promoting activity in a vascular endothelial cell-specific manner in a hypoxic state can be mentioned. Here, the "stringent conditions" means a condition where a nucleotide sequence having a homology of not less than 80% to the nucleotide sequence shown in SEQ ID NO: 1 hybridizes. Preferable examples include conditions where DNA consisting of a nucleotide sequence having a homology of not less than 90%, more preferably not less than 95%, to the nucleotide sequence shown in SEQ ID NO: 1 hybridizes. The homology of the nucleotide sequence in the present specification can be calculated using homology calculation algorithm NCBI BLAST (National Center for Biotechnology Information Basic Local Alignment Search Tool) under the following conditions (expectancy=10; gap accepted; filtering=ON; match score=1; mismatch score=−3). Specific examples of the "stringent conditions" include the conditions described in Molecular Cloning: A Laboratory Manual 2nd ed. (edited by T. Maniatis et al., Cold Spring Harbour Laboratories, 1989) and the like, for example, hybridization reaction in 6×SSC (sodium chloride/sodium citrate) at 45° C., followed by washing one or more times in 0.2×SSC/0.1% SDS at 65° C. and the like. Those of ordinary skill in the art can readily adjust to a desired stringency by appropriately changing the salt concentration of hybridization solution, temperature of hybridization reaction, probe concentration, probe length, mismatch number, hybridization reaction time, salt concentration of washing solution, temperature of washing and the like.

Examples of other "substantially the same nucleotide sequence" include a nucleotide sequence corresponding to the nucleotide sequence shown in SEQ ID NO: 1 in an ADAMTS-1 gene promoter derived from mammals other than human (e.g., mouse, rat, rabbit, guinea pig, hamster, bovine, horse, sheep, monkey, dog, cat etc.), a part thereof containing at least one HRE consensus sequence and the like. The sequence information of orthologs in other mammals can be obtained by a search of the database of genome and/or cDNA of mammals other than human using BLAST and FASTA and the nucleotide sequence shown in SEQ ID NO: 1 as a query, or, for example, by a search of Mouse Genome Informatics (http://www.informatics.jax.org/) provided by Jackson Laboratories using accession No. and gene symbol/gene name as keywords, and accessing to the information of Mammalian Orthology in the caught data and the like.

The vascular endothelial cell in which gene transcription can be promoted transiently in a hypoxic state by the DNA of the present invention may be any and examples thereof include, but are not limited to, umbilical cord intravenous endothelial cell, coronary endothelial cell, brain vascular endothelial cell, aortic endothelial cell, pulmonic artery endothelial cell, superior mesenteric artery endothelial cell, kidney artery endothelial cell and the like.

The "transcription promoting activity" in the present specification means an ability to transiently promoting, in cooperation with a basal promoter sequence such as TATA box and the like, transcription of a gene placed at the downstream thereof in a vascular endothelial cell-specific manner in a hypoxic state, and the DNA of the present invention also encompasses those without having a basal promoter activity in themselves.

The DNA of the present invention may be a physiologically acceptable salt with an acid or a base and, for example, a physiologically acceptable acid addition salt is preferable. Useful salts include, for example, salts with inorganic acids (for example, hydrochloric acid, phosphoric acid, hydrobromic acid, sulfuric acid) or salts with organic acids (for example, acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The DNA of the present invention can be prepared from genome DNA extracted from any cell (for example, hepatocyte, splenocyte, nerve cell, glial cell, pancreatic β cell, myelocyte, mesangial cell, Langerhans' cell, epidermal cell, epithelial cell, endothelial cell, fibroblast, fibrocyte, myocyte, adipocyte, immune cell (for example, macrophage, T cell, B cell, natural killer cell, mast cell, neutrophil, basophil, eosinophil, monocyte), megakaryocyte, synovial cell, chondrocyte, bone cell, osteoblast, osteoclast, mammary gland cell or interstitial cell, or corresponding precursor cell, stem cell or cancer cell thereof, and the like) derived from a human or other mammal (e.g., mouse, rat, rabbit, guinea pig, hamster, bovine, horse, sheep, monkey, dog, cat etc.) or any tissue where such cells are present (for example, brain or any portion of brain (e.g., olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gallbladder, bone marrow, adrenal gland, skin, muscle, lung, gastrointestinal tract (e.g., large intestine, small intestine), blood vessel, heart, thymus, spleen, salivary gland, peripheral blood, prostate, testicle, ovary, placenta, uterus, bone, cartilage, joint and the like), by cloning a genomic DNA comprising the promoter region with a publicly known ADAMTS-1 gene promoter sequence as a probe, cleaving the DNA into a DNA fragment comprising the desired partial promoter sequence using a DNA degradation enzyme, for example, an appropriate restriction enzyme, separating the fragment by gel electrophoresis, thereafter recovering the desired band, and purifying the DNA. Alternatively, an ADAMTS-1 promoter partial sequence can be amplified and isolated by a PCR using a primer synthesized on the basis of a the nucleotide sequence shown by SEQ ID NO:1 with a crude extract of the above-described cell or a genomic DNA isolated therefrom as a template.

In addition, the DNA of the present invention can also be obtained by chemical synthesis on the basis of the nucleotide sequence shown by SEQ ID NO: 1 using a commercially available DNA/RNA synthesizer.

The present invention also provides an expression vector containing a promoter containing the above-mentioned DNA of the present invention, which is capable of transiently expressing a gene operably linked to the promoter in a vascular endothelial cell-specific manner in a hypoxic state.

When the DNA of the present invention contains a basal promoter sequence such as TATA box and the like (nucleotides 1551-1554 of SEQ ID NO: 1 contains estimated TATA box), the DNA itself can be used as a promoter. When the DNA does not contain the basal promoter sequence, a nucleotide sequence conferring a basal promoter activity derived from other known expression promoter for mammals, for example, SRα promoter, SV40 promoter, LTR promoter, CMV (cytomegalovirus) promoter, HSV-tk promoter and the like, is added. Furthermore, another transcription control cis-sequence (e.g., CAAT box, GC box and the like) can also be placed at an appropriate position.

Useful vectors include plasmids derived from *E. coli* (e.g., pBR322, pBR325, pUC12, pUC13); plasmids derived from *Bacillus subtilis* (e.g., pUB110, pTP5, pC194); plasmids derived from yeast (e.g., pSH19, pSH15); bacteriophages such as λ phage; retrovirus, vaccinia virus and animal viruses such as baculovirus; pA1-11, pXT1, pRc/CMV, pRc/RSV, pcDNAI/Neo and the like.

Useful vectors of the present invention include, in addition to the above, expression vectors that optionally comprises a splicing signal, a polyA addition signal, a selection marker, a replication origin and the like. Poly A addition signal is preferably connected to the downstream of the promoter containing the DNA of the present invention via a multicloning site. As examples of the selection markers, the dihydrofolate reductase (hereinafter also abbreviated as dhfr) gene [methotrexate (MTX) resistance], the ampicillin resistance gene (hereinafter also abbreviated as Amp$^r$), the neomycin resistance gene (hereinafter also abbreviated as Neo$^r$, G418 resistance), and the like can be mentioned.

In addition, where necessary, a nucleotide sequence encoding a signal sequence (signal codon) may be added between the promoter and poly A addition signal to give a secretion expression vector. Examples of usable signal sequences include insulin signal sequence, α-interferon signal sequence, antibody molecule signal sequence and the like.

The vector of the present invention can be constructed by appropriately connecting each of the above-mentioned vector constituent elements by a conventional known genetic engineering using restriction enzyme and ligase.

As mentioned above, since the DNA of the present invention can transiently promote gene transcription in a vascular endothelial cell-specific manner preferably in a period corresponding to acute ischemia as a hypoxic state that occurs in an animal individual, the vector of the present invention containing a promoter containing the DNA is preferably an acute ischemic stage-specific expression vector.

Since the vector of the present invention can transiently promote gene transcription in a vascular endothelial cell-specific manner, preferably acute ischemia stage-specifically, in a hypoxic state, by administering a vector obtained by operably connecting a gene encoding a protein or RNA (e.g., antisense RNA, siRNA etc.) capable of preventing and/or treating a disease by expression in the vascular endothelial cell in a hypoxic state (to be also simply referred to as "gene for prophylaxis and/or treatment") to the downstream of the promoter of the vector, to a mammal, preferably human, in need of the prophylaxis and/or treatment of the disease, the disease can be prevented and/or treated.

Therefore, the present invention provides an agent for the prophylaxis and/or treatment of a disease associated with a hypoxic state of vascular endothelial cells, which comprises the above-mentioned vector of the present invention. Here, examples of the "disease associated with a hypoxic state of vascular endothelial cells" include a disease developed by a hypoxic state caused by an abrupt stoppage of the blood supply to tissues due to obstruction, sclerosis, convulsion of blood vessel, blood circulation disorder and the like (generically referred to as an "acute ischemic disease" in the present specification), cancer showing a hypoxic state as an internal environment, particularly cancer in a growth stage, and the like. Specific examples of the acute ischemic disease include ischemic cardiac diseases (unstable angina pectoris, myocardial infarction, acute coronary syndrome and the like), ischemic brain diseases (cerebral infarction, TIA and the like), ischemic lung disease (lung infarction and the like), kidney infarction, acute mesenteric artery obstruction, acute artery obstruction, retina artery obstruction, retina intravenous obstruction, ischemic bowel disease (ischemic colitis and the like) and the like. Furthermore, the "disease associated with a hypoxic state of vascular endothelial cells" also includes ischemia reperfusion disorder after organ transplantation.

Examples of the gene for the prophylaxis and/or treatment of the present invention, that is, a gene capable of preventing and/or treating a disease associated with a hypoxic state of vascular endothelial cells, preferably an acute ischemic disease, include genes relating to so-called angiogenesis such as VEGF, erythropoietin, hepatocyte growth factor (HGF), basic fibroblast growth factor (basic FGF), endothelial-derived nitric oxide synthase (eNOS), Integrin-linked kinase, Mcl-1 and the like, genes having an anti-apoptosis action (for example, Bcl-2, Bcl-xL, Bcl-w, Mcl-1 and the like), a gene segment binding to NF-κB that expresses oxidation stress response gene, ischemia resistance gene and the like. Since the nucleotide sequences of these genes are all known, a gene for the prophylaxis and/or treatment can be directly amplified by Polymerase Chain Reaction (hereinafter to be abbreviated as "PCR method") or Reverse Transcriptase-PCR (hereinafter to be abbreviated as "RT-PCR method") using a primer produced based on the nucleotide sequence, and a genome DNA fraction or total RNA or mRNA fraction as a template, which is prepared from a cell, tissue or organ derived from human or other mammal. Alternatively, a gene for the prophylaxis and/or treatment can also be cloned from a genome DNA library or cDNA library prepared by inserting the above-mentioned genome DNA or total RNA or mRNA fragment prepared from a cell, tissue or organ into a suitable vector, by colony or plaque hybridization method, PCR method or the like. The vector to be used for the library may be any from bacteriophage, plasmid, cosmid, phagemid and the like.

By digesting the obtained gene for the prophylaxis and/or treatment with a suitable restriction enzyme, and ligating the gene to the vector of the present invention cleaved between the promoter and polyA addition signal by using a ligase in the same manner, a vector wherein the gene for the prophylaxis and/or treatment is operably linked can be produced.

Since the vector of the present invention can transiently promote gene transcription in a vascular endothelial cell-specific manner, preferably acute ischemia stage-specifically, in a hypoxic state, the vector transferred into cells other than endothelial cells cannot express a gene for the prophylaxis and/or treatment. As a result, a product of the gene for the prophylaxis and/or treatment affords an effect similar to that obtained by selective and transient delivery to vascular endothelial cells in a hypoxic state.

Hence, in one aspect, the present invention also provides a drug delivery system comprising the vector of the present invention, which can selectively deliver a product of the gene for the prophylaxis and/or treatment to vascular endothelial cells in a hypoxic state.

When the vector of the present invention is used as a prophylactic or therapeutic agent for a disease associated with a hypoxic state of vascular endothelial cells, the vector alone, or after insertion to an appropriate vector such as the retrovirus vector, adenovirus vector, lentivirus vector, adeno-associated virus vector and the like, can be formulated according to a conventional method. The vector, as is or along with an auxiliary agent for promotion of intake thereof, can be administered using a gene gun or a catheter like a hydrogel catheter.

For example, the vector can be used orally as tablets coated with sugar, capsules, elixirs, microcapsules and the like, as required, or can be used non-orally in the form of an injection such as a sterile solution or suspension in water or another pharmaceutically acceptable liquid. For example, by blending the vector along with a known physiologically acceptable carrier, a sweetener, a excipient, a vehicle, an antiseptic, a stabilizer, a binder and the like, in a unit dosage form required for generally accepted preparation design, such a preparation can be produced. The active ingredient contents in these preparations are intended to ensure that an appropriate dose in the specified range is obtained.

As examples of additives that can be formulated in tablets, capsules and the like, a binder like gelatin, cornstarch, tragacanth and gum arabic, a excipient like crystalline cellulose, a swelling agent like cornstarch, gelatin, alginic acid and the like, a lubricant like magnesium stearate, a sweetener like sucrose, lactose or saccharin, a flavoring agent like peppermint, acamono oil or cherry and the like can be used. When the formulation unit form is a capsule, the above-described type of material can further contain a liquid carrier like an oil or fat. A sterile composition for injection can be formulated according to an ordinary preparation design such as dissolving or suspending an active substance, a naturally produced vegetable oil such as sesame oil or coconut oil, and the like in a vehicle like water for injection. As examples of aqueous solutions for injection, physiological saline, an isotonic solution containing glucose or other auxiliary agent (for example, D-sorbitol, D-mannitol, sodium chloride and the like) and the like can be used, which may be used in combination with an appropriate solubilizer, for example, an alcohol (e.g., ethanol), a polyalcohol (e.g., propylene glycol, polyethylene glycol), a non-ionic surfactant (e.g., polysorbate 80™, HCO-50) and the like. As examples of oily solutions, sesame oil, soybean oil and the like can be used, which may be used in combination with a solubilizer such as benzyl benzoate, benzyl alcohol and the like.

Also, the above-described prophylactic or therapeutic agent may be formulated with, for example, a buffering agent (for example, phosphate buffer solution, sodium acetate buffer solution), a soothing agent (for example, benzalkonium chloride, procaine hydrochloride and the like), a stabilizer (for example, human serum albumin, polyethylene glycol and the like), a preservative (for example, benzyl alcohol, phenol and the like), an antioxidant and the like. The prepared injection solution is normally filled in an appropriate ampoule.

Because the preparation thus obtained is safe and of low toxicity, it can be administered to, for example, a human or other mammals (for example, rat, mouse, hamster, rabbit, sheep, goat, swine, bovine, horse, cat, dog, monkey, chimpanzee and the like).

The dosage of the vector of the present invention varies depending on subject of administration, target organ, symptoms, method of administration and the like; in a patient with myocardial infarction (body weight 60 kg), for example, the usual oral dosage is about 0.1 mg to 100 mg, preferably about 1.0 to 50 mg, more preferably about 1.0 to 20 mg, per day. In the case of non-oral administration, the dosage per administration varies depending on subject of administration, target organ, symptoms, method of administration and the like; in a patient with myocardial infarction (body weight 60 kg), for example, it is convenient that the usual dosage in an injection is about 0.01 to 30 mg, preferably about 0.1 to 20 mg, more preferably about 0.1 to 10 mg, per day. In the case of another animal, a dosage converted per 60 kg body/human weight can be administered.

On the other hand, when a reporter gene is operably connected to the downstream of the promoter of the vector of the present invention, and the vector is transferred into a cell or tissue of a mammal or individual mammal, since the reporter gene is specifically expressed in vascular endothelial cells in the initial stage of a particular period in a hypoxic state, preferably a hypoxic state represented by acute ischemia stage, vascular endothelial cells in a hypoxic state, particularly acute ischemia stage, can be detected by detecting a reporter protein encoded by the reporter gene.

Therefore, the present invention also provides a reagent for detecting vascular endothelial cells in a hypoxic state, comprising the vector of the present invention wherein a reporter gene is operably linked.

Examples of the reporter gene to be used for the detection reagent of the present invention include, but are not limited to, a gene encoding luciferase, GFP, peroxidase, alkali phosphatase and the like. In consideration of the object of rapidly detecting vascular endothelial cells in a hypoxic state, particularly in an acute ischemia stage, a reporter gene capable of diagnostic imaging is particularly preferable. For example, when a luciferase gene is used as a reporter gene, the detection reagent of the present invention is administered to a mammal the vector of the present invention, then luciferin is administered to the animal, and chemical luminescence is visualized as digital images using a realtime in vivo imaging apparatus equipped with an ultrasensitive cooling CCD camera (e.g., IVIS200 of Summit Pharmaceuticals International Corporation, and the like), whereby vascular endothelial cells in a hypoxic state can be easily detected.

Preferably, the reagent for detection of the present invention is administered to a mammal affected with a disease associated with a hypoxic state of vascular endothelial cells, effectively acute ischemic disease, or suspected to be affected therewith in the future, preferably human, whereby the reagent can be used as a diagnostic drug for the disease. Therefore, preferably in the same manner as in the aforementioned prophylactic or therapeutic agent of the present invention, the detection reagent of the present invention can be formulated into a preparation by treating the vector alone, or after insertion into an appropriate vector such as retrovirus vector, adenovirus vector, lentivirus vector, adeno-associated virus vector and the like according to a conventional means. The vector, as is or along with an auxiliary agent for promoting intake thereof, can be administered using a gene gun or a catheter like a hydrogel catheter. The administration route and dose can also be determined according to those of the aforementioned prophylactic or therapeutic agent of the present invention.

As mentioned above, in a cell or tissue of a mammal or individual mammal, into which the vector of the present invention with an operably-linked reporter gene is transferred, vascular endothelial cells in a hypoxic state, particularly acute ischemia stage, can be easily detected by monitoring the expression of the reporter gene. Therefore, a transgenic animal, into which the vector has been transferred, can be preferably used as an animal material for producing an animal model in a hypoxic state or with an acute ischemic disease.

The transgenic (Tg) animal of the present invention is produced by transferring the vector of the present invention to a fertilized ovum, an unfertilized ovum, a sperm, or a precursor cell thereof (primordial germ cell, oogonium, oocyte, ovum, gonocyte, spermatocyte, spermatid and the like) or the like of non-human animal, preferably in the early stage of embryogenesis in fertilized ovum (more preferably, at or prior to the 8-cell stage), by the gene transfer method such as calcium phosphate method, the electric pulse (electroporation) method, the lipofection method, the aggregation method, the microinjection method, the particle gun method, the DEAE-dextran method and the like. Also, it is possible to transfer the vector to a somatic cell, a tissue, an organ or the like of non-human mammal by the gene transfer method, and utilize it for cell culture, tissue culture and the like; furthermore, it is also possible to produce the transgenic animal by fusing these cells with the above-described embryonic (or germ) cell by a method of cell fusion known per se.

A part of the living body of the transgenic animal produced in this manner can be used for the same purpose as an individual Tg animal. Preferable examples of the part of the living body of the transgenic animal of the present invention include organs such as the liver, heart, kidney, adrenal gland, blood vessels, gastrointestinal tract and brain, and tissues and cells derived from these organs, and the like.

The "non-human mammal" that can be used as the subject of the present invention is not particularly limited as long as it is a non-human mammal for which a transgenic system has been established and, for example, bovine, monkey, swine, sheep, goat, rabbit, dog, cat, guinea pig, hamster, rat, mouse and the like can be mentioned. Preferred are rabbit, dog, cat, guinea pig, hamster, mouse, rat and the like, and particularly preferred from the viewpoint of preparation of a disease animal model are rodents, which have relatively short ontogenesis and biological cycles, and which permit easy propagation, particularly the mouse (for example, C57BL/6 strain, DBA2 strain and the like as pure strains, B6C3F$_1$ strain, BDF$_1$ strain, B6D2F$_1$ strain, BALB/c strain, ICR strain and the like as cross strains) or the rat (for example, Wistar, SD and the like) and the like.

Also, in addition to mammals, birds such as chicken can be used for the same purpose as that of a "non-human mammal" that is the subject of the present invention.

In a preferred embodiment, the vector of the present invention is transferred to an early embryo of the subject non-human mammal by the microinjection method.

An early embryo of the subject non-human mammal can be obtained by collecting an internally fertilized egg obtained by mating a female and a male of the same species of non-human mammal, or by externally fertilizing an ovum and sperm collected from a female and a male, respectively, of the same species of non-human mammal.

The age, rearing conditions and the like for the non-human mammal used vary depending on the animal species; when using the mouse (preferably an inbred mouse such as C57BL/6J (B6), F$_1$ of B6 and another inbred strain, and the like), for example, it is preferable that the female be at about 4 to about 6 weeks of age, and the male be at about 2 to about 8 months or so of age, and is also preferable that they be reared under about 12-hour bright phase conditions (for example, 7:00-19:00) for about 1 week.

Although internal fertilization may be by spontaneous mating, a method wherein for the purpose of regulating the sexual cycle and obtaining a large number of early embryos from one animal, gonadotropin is administered to a female non-human mammal to induce superovulation, and thereafter the female is mated with a male non-human mammal, is preferred.

As examples of the method of inducing ovulation in a female non-human mammal, a method wherein follicle-stimulating hormone (pregnant mare's serum gonadotropin, generally abbreviated as PMSG) is first administered, then luteinizing hormone (human chorionic gonadotropin, generally abbreviated as hCG) is administered, by, for example, intraperitoneal injection and the like, is preferred; the preferable hormone dosage and administration interval respectively vary depending on the species of non-human mammal. For example, when the non-human mammal is the mouse (preferably an inbred mouse such as C57BL/6J (B6), $F_1$ of B6 and another inbred strain, and the like), a method wherein a fertilized egg is obtained by administering luteinizing hormone at about 48 hours after administration of follicle-stimulating hormone, and thereafter immediately mating the female with a male mouse, is usually preferred; the dosage of follicle-stimulating hormone is about 20 to about 50 IU/animal, preferably about 30 IU/animal, and the dosage of luteinizing hormone is about 0 to about 10 IU/animal, preferably about 5 IU/animal.

After a given time has elapsed, the peritoneum of each female non-human mammal confirmed by vaginal plug testing and the like to have copulated was incised, and fertilized eggs are taken out from the oviduct, washed in a medium for embryo culture (e.g., M16 medium, modified Whitten medium, BWW medium, M2 medium, WM-HEPES medium, BWW-HEPES medium and the like) to remove cumulus cells, and cultured by the droplet culture method and the like in the presence of 5% carbon dioxide/95% atmosphere until the time of DNA microinjection. When microinjection is not immediately conducted, it is also possible to preserve the collected fertilized eggs under freezing by the slow method or the ultrarapid method and the like.

On the other hand, in the case of external fertilization, follicle-stimulating hormone and luteinizing hormone are administered to a female non-human mammal for egg collection (the same as in the case of internal fertilization is preferably used) in the same manner as above to induce ovulation, after which eggs are collected and cultured in a medium for fertilization (e.g., TYH medium) until the time of external fertilization by the droplet culture method and the like in the presence of 5% carbon dioxide/95% atmosphere. On the other hand, the tail of the epididymis is taken out from the same species of male non-human mammal (the same as in the case of internal fertilization is preferably used), and a sperm mass is collected and pre-cultured in a medium for fertilization. After completion of the pre-culture, the sperm is added to an egg-containing medium for fertilization; after cultivation by the droplet culture method and the like in the presence of 5% carbon dioxide/95% atmosphere, fertilized eggs having two pronuclei are selected under a microscope. When DNA microinjection is not immediately conducted, it is also possible to preserve the collected fertilized eggs under freezing by the slow method or the ultrarapid method and the like.

DNA microinjection to a fertilized egg can be performed using a publicly known apparatus such as a micromanipulator according to a conventional method. Briefly speaking, the fertilized egg placed in a droplet of a medium for embryo culture is aspirated using a holding pipette and immobilized, and a DNA solution is injected directly to the male or female pronucleus, preferably into the male pronucleus, using an injection pipette. The transferred DNA used is preferably one that has been highly purified by CsCl density gradient ultracentrifugation and the like. Also, the transferred DNA is preferably linearized by cutting the vector portion thereof using a restriction enzyme.

After the DNA transfer, the fertilized egg is cultured in a medium for embryo culture by the droplet culture method and to the like in the presence of 5% carbon dioxide/95% atmosphere until the 1-cell stage—blastocyst stage, after which it is transplanted into the oviduct or uterus of a female non-human mammal for embryo reception rendered to be pseudopregnant. The female non-human mammal for embryo reception may be any female, as long as it is of the same species as the animal from which the early embryo to be transplanted is derived; for example, when a mouse early embryo is transplanted, a female ICR strain mouse (preferably about 8 to about 10 weeks of age) and the like are preferably used. As an example of the method of rendering the female non-human mammal for embryo reception to be in a pseudopregnant state, a method wherein the female is mated with the same species of vasectomized (ligated) male non-human mammal (for example, in the case of a mouse, a male ICR strain mouse (preferably about 2 months or more of age)), and selecting one confirmed as having a vaginal plug, is known.

The female for embryo reception used may be a spontaneously ovulating female, or a female having fertility induced by administering luteinizing hormone-releasing hormone (generally abbreviated as LHRH) or an analog thereof prior to mating with a vasectomized (ligated) male. As examples of the LHRH analog, [3,5-DiI-Tyr$^5$]-LH-RH, [Gln$^8$]-LH-RH, [D-Ala$^6$]-LH-RH, [des-Gly$^{10}$]-LH-RH, [D-His (Bzl)$^6$]-LH-RH, Ethylamides thereof and the like can be mentioned. The dosage of LHRH or an analog thereof, and the timing of mating with a male non-human mammal after administration thereof vary depending on the species of non-human mammal. For example, when the non-human mammal is the mouse (preferably an ICR strain mouse and the like), it is usually preferable that the female mouse be mated with a male mouse at about 4 days after LHRH or an analog thereof is administered; the dosage of LHRH or an analog thereof is usually about 10 to 60 µg/animal, preferably about 40 µg/animal.

Usually, when the early embryo to be transplanted is in the morula stage or after, it is transplanted to the uterus of a female for embryo reception; when the early embryo is in an earlier stage (for example, 1-cell stage to 8-cell stage embryo), it is transplanted to the oviduct. As the female for embryo reception, one which is older than a given number of days from pseudopregnancy, depending on the developmental stage of the transplanted embryo, is appropriately used. For example, in the case of the mouse, a female mouse at about 0.5 days after pseudopregnancy is preferred for transplantation of a 2-cell stage embryo, and a female mouse at about 2.5 days after pseudopregnancy is preferred for transplantation of a blastocystic embryo. After the female for embryo reception is anesthetized (preferably Avertin, Nembutal and the like are used), an incision is made, the ovary is drawn out, early embryo (about 5 to about 10 cells) in suspension in a medium for embryo culture are injected to the peritoneal opening of the oviduct or the vicinity of the oviduct junction of the uterine horn using a pipette for embryo transplantation.

If the transplanted embryo successfully implants and the embryo recipient female becomes pregnant, non-human mammal animals are obtained by spontaneous delivery or caesarian section. Embryo recipient females that delivered spontaneously are allowed to continue suckling; if the animals are delivered by caesarian section, the animals can be suckled by a separately provided female for suckling (for example, in the case of the mouse, a female mouse with usual mating and delivery (preferably female ICR strain mouse and the like)).

Referring to the introduction of DNA in the fertilized egg cell stage, it is assured that the transferred DNA is present in all germ line cells and somatic cells of the subject non-human mammal. Whether or not the transferred DNA is incorporated in the chromosome DNA can be determined by, for example, screening chromosome DNAs separated and extracted from the tails of offspring animals, by Southern hybridization or PCR method. The presence of the vector the present invention in the germ line cells of non-human mammal animals ($F_0$) obtained as described above means that a reporter gene under the control of a promoter comprising the DNA of the present invention is present in all of the germ line cells and somatic cells of all progeny ($F_1$) animals.

Usually, the $F_0$ animals are obtained as heterozygotes having the transferred DNA in only one of the homologous chromosomes. Also, transferred DNA is randomly inserted onto different chromosomes in individual $F_0$ animals unless produced by homologous recombination. To obtain a homozygote having the transferred DNA on both homologous chromosomes, an $F_0$ animal and a non-transgenic animal are crossed to prepare $F_1$ animals, and siblings of a heterozygote having the transferred DNA in only one of the homologous chromosomes are crossed. Provided that the transferred DNA has been incorporated in only one gene locus, one-fourth of the obtained $F_2$ animals would be homozygotes.

An ischemic disease model can be produced by applying a surgical method such as blood vessel ligation and the like to the Tg animal of the present invention obtained as mentioned above. In addition, while a tumor-bearing animal can be easily produced from mouse and the like, since a cancer tissue has a hypoxic state as an internal environment, the Tg animal is useful for rapidly detecting or identifying a carcinogenesis part in a cancer-induced model.

EXAMPLES

The present invention is explained in more detail in the following by referring to Reference Example and Examples. The following shows representative Reference Example and Examples, which are not limitative and permit various applications within the range not deviating from the technical idea of the present invention.

Reference Example

Detection of ADAMTS-1 mRNA in Cultured Cells in a Hypoxic State (1) Cell Culture Human umbilical vein endothelial cell (HUVEC) was cultured in EBM-2 medium (manufactured by CAMBREX) containing 2% FCS, human retinal pigment epithelial cell (ARPE) was cultured in DMEM medium (manufactured by Sigma Ltd.) containing 10% FCS, human skin fibroblast was cultured in DMEM medium (manufactured by Sigma Ltd.) containing 10% FCS, human cardiac muscle fibroblast line (H9C2) was cultured in DMEM medium (manufactured by Sigma Ltd.) containing 10% FCS, monkey kidney cell line (COS7) was cultured in DMEM medium (manufactured by Sigma Ltd.) containing 10% FCS, mouse artery smooth muscle cell line (SMC) was cultured in DMEM medium (manufactured by Sigma Ltd.) containing 10% FCS, human microvascular endothelial cell (HMVEC) was cultured in EBM-2 medium (manufactured by CAMBREX) containing 2% FCS, and human lung artery endothelial cell (HPAEC) was cultured in EBM-2 medium (manufactured by CAMBREX) containing 2% FCS.

(2) Low Oxygen Culture and Extraction of ADAMTS-1 mRNA

The above-mentioned cells ($3 \times 10^5$) were cultured in a carbon dioxide incubator to subconfluent, and the incubator was filled with nitrogen gas to produce a hypoxic state (1% $O_2$).

Each cell was cultured for 1 hr, 3 hr, 6 hr and 24 hr (as to HCAEC, further 48 hr and 72 hr), and RNA was extracted by the AGPC method.

(3) Measurement of ADAMTS-1 mRNA Expression Amount

The mRNA expression level of ADAMTS-1 was measured by realtime PCR method using a LightCycler rapid thermal cycler system (manufactured by Roche). In detail, cDNA was synthesized using mRNA as template and using reverse transcriptase (SS-II, Invitrogen), ADAMTS-1 specific primer m was designed, and a realtime PCR reaction was performed. Using α tubeline or β-actin as an internal standard, the mRNA expression level was amended and quantified.

```
Upper primer:
CACTCTGCGGAACTTTTGC,       (SEQ ID NO: 2)
or

CTCCGGTGGCTTAGTGGTGT       (SEQ ID NO: 3)

Lower primer:
GCATCATCATGTGGCATGTTA,     (SEQ ID NO: 4)
or

TGTTTTTCCGTTATTGTCTG       (SEQ ID NO: 5)
```

Figures 1, 3:
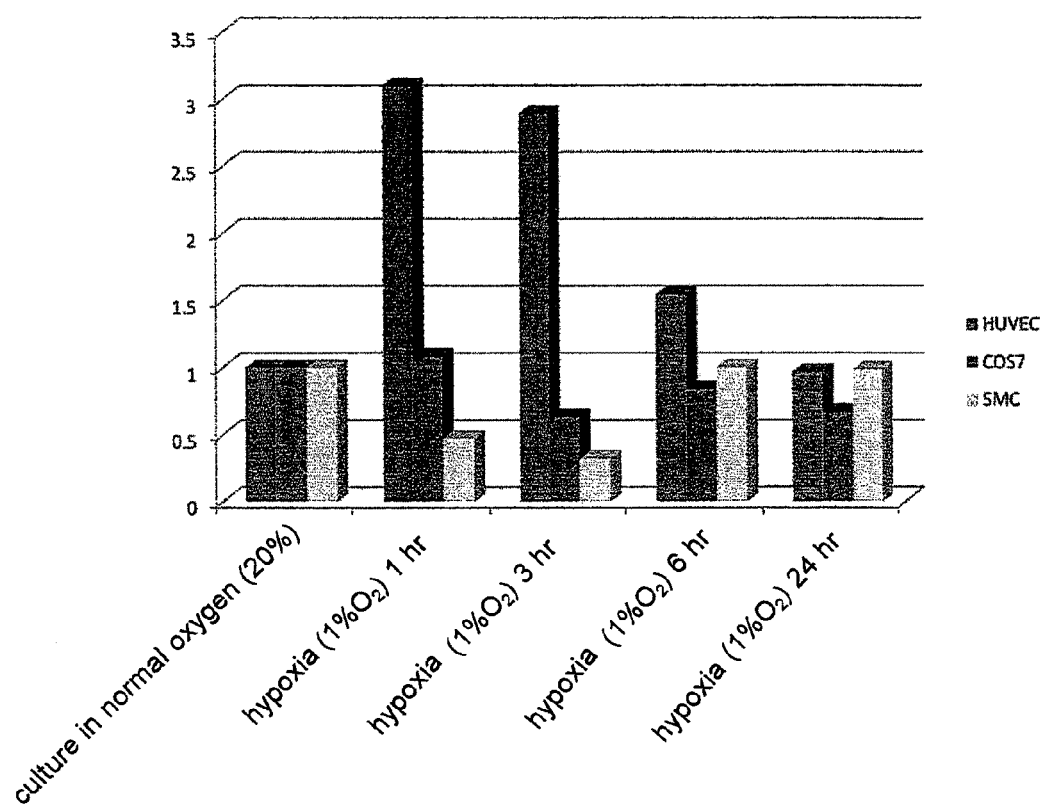
Figures 2, 3:
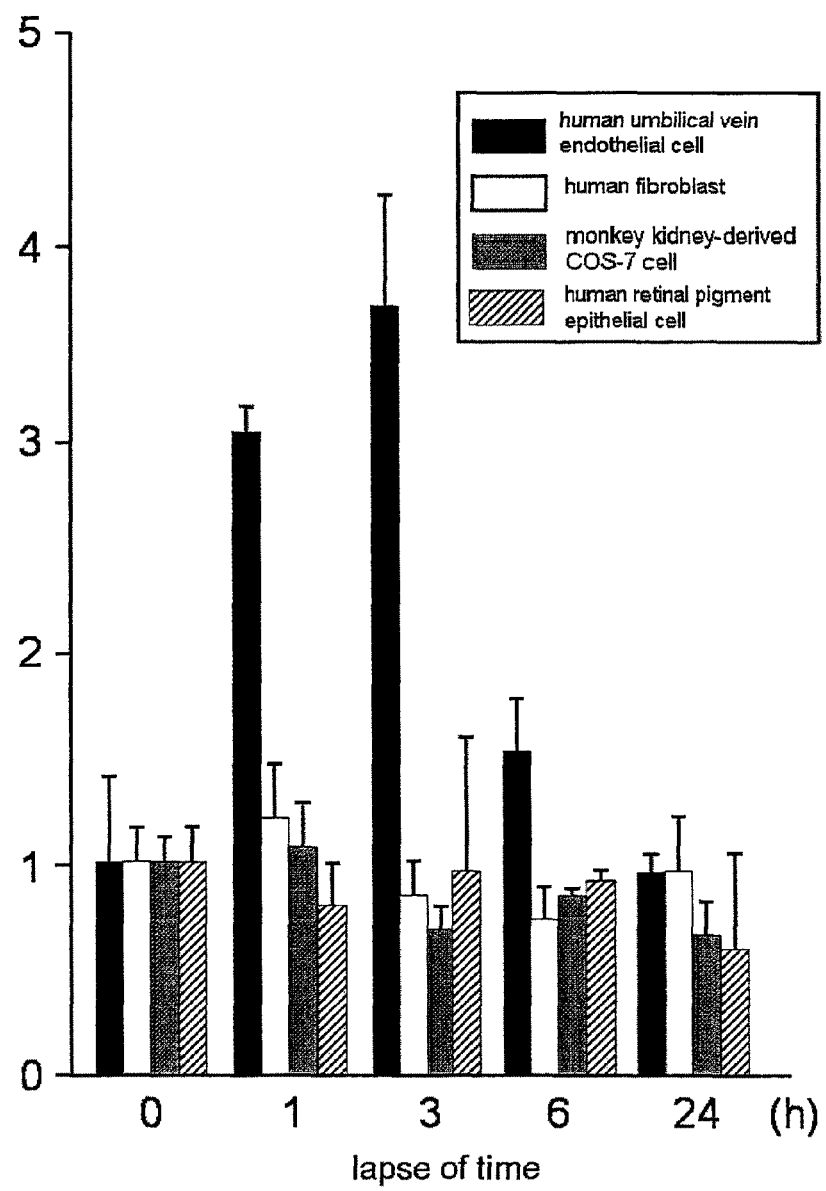
Figure 4:
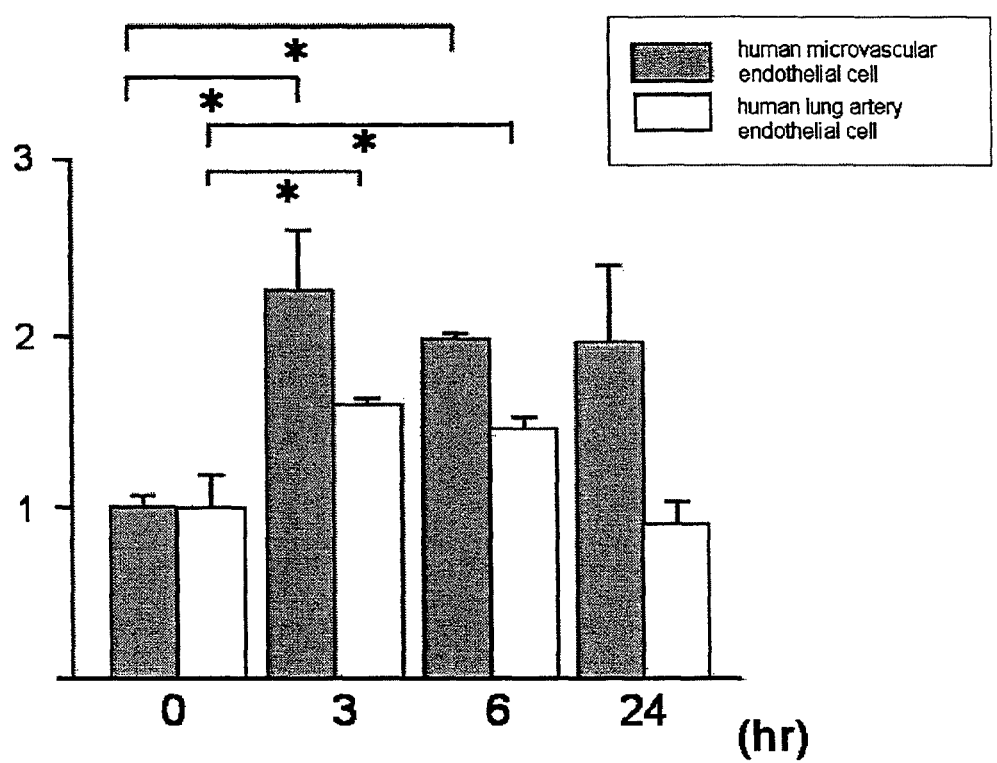
FIG. 4 shows expression of ADAMTS-1 in various cells in a low oxygen state: human microvascular endothelial cell (HMVEC); human pulmonic artery endothelial cell (HPAEC) from the left.

The results are shown in FIGS. 1-4. ADAMTS-1 showed enhanced expression in vascular endothelial cells in a hypoxic state. (FIG. 1 and FIG. 3). That is, when HUVEC was used, the expression was found to have been markedly enhanced in a hypoxic state in the acute stage (1 hr-3 hr) (FIG. 1). In addition, it was found that the expression was markedly enhanced in a hypoxic state in the acute stage (3 hr) even when human microvascular endothelial cells or human lung artery endothelial cells were used (FIG. 4; in FIG. 4, the mark * means P<0.05). On the other hand, the expression level of ADAMTS-1 in a hypoxic state did not differ much in the cells of other tissues (FIG. 2 and FIG. 3). From the above, it was clarified that the expression of ADAMTS-1 was enhanced in various vascular endothelial cells in a hypoxic state.

Example 1

Identification of Region in ADAMTS-1 Promoter, Having Acute Ischemia Stage- or Vascular Endothelial Cell-Specific Transcription Promoting Activity (1) Cloning of ADAMTS-1 Promoter Fragment Since the presence of ADAMTS1 in chromosome 21q is known from human genomic DNA database, the upstream of the initiation codon thereof was considered as a promoter region. A primer was designed from the database, PCR was performed and cloned to TA vector, and the nucleotide sequence was confirmed. The nucleotide sequence is shown in FIG. 5.

Figure 6:
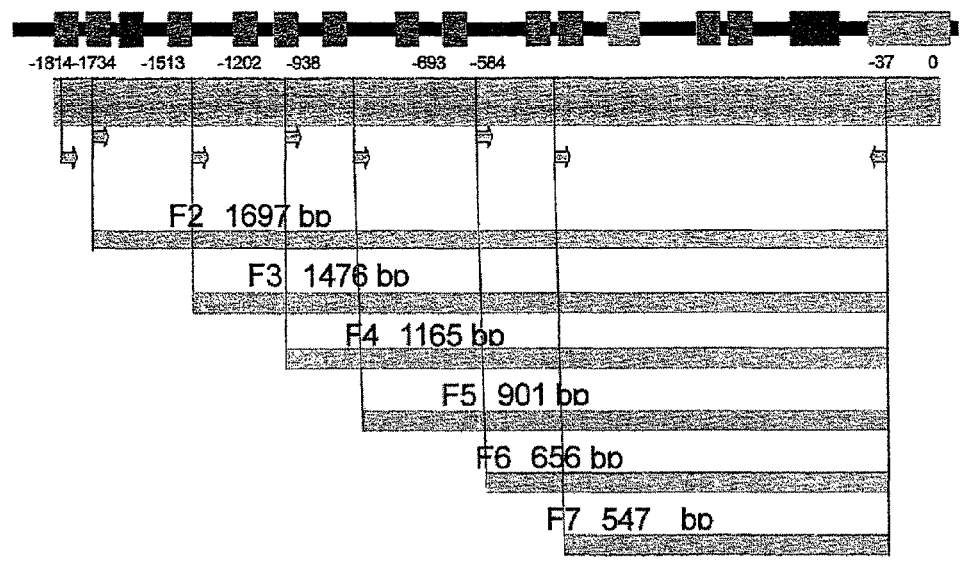
FIG. 6 is a schematic diagram showing ADAMTS-1 promoter fragments with various lengths.

(2) Production of Reporter Plasmid Containing Various Lengths of ADAMTS-1 Promoter Fragment 7 kinds of ADAMTS-1 promoter fragments having different lengths as shown in FIG. 6 were produced. Each primer was designed from the database, PCR was performed and TA cloning was performed. The sequence was confirmed to verify absence of mutation, and promoter DNA having each length was inserted into pMetLuc-Reporter (Clontech) at the restriction enzyme site of EcoRI-EcoRI.

Figure 7:
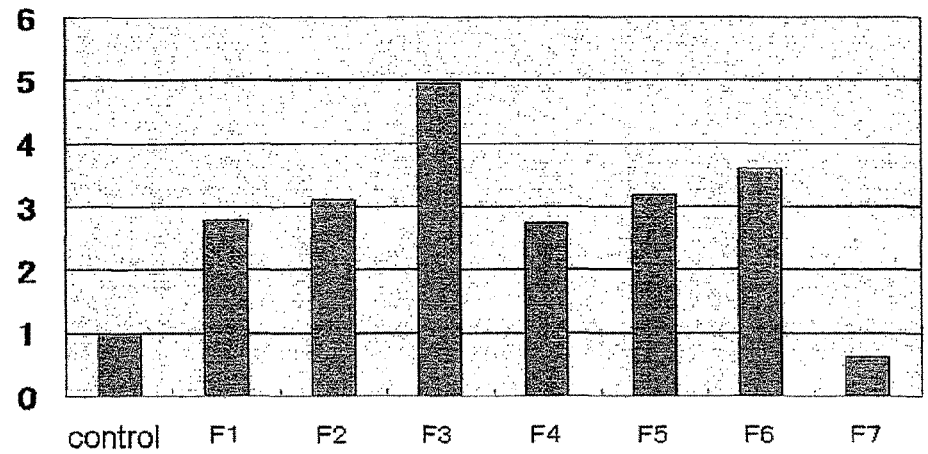
FIG. 7 shows promoter activity of ADAMTS-1 promoter fragments with various lengths in HUVEC in a low oxygen state. Each construct is shown in FIG. 6. (F1 is −1814 to −37)

(3) Identification of Region Having Acute Ischemia Stage- or Vascular Endothelial Cell-Specific Transcription Promoting Activity The 7 kinds of reporter plasmids containing ADAMTS-1 promoter fragments having different lengths, which were produced in the above-mentioned (2), were each transferred into endothelial cells according to the electroporation method, and the culture medium was exchanged 18 hr later. After a normoxic state (20% $O_2$) for 24 hr, the culture supernatant was collected (normoxia-medium), exchanged with a new culture supernatant, and set in a hypoxic state for 24 hr. The culture supernatant was collected (hypoxia-medium). 1×Substrate/Reaction buffer contained in Ready-To-Glow™ Secreted Luciferase Reporter System of Clontech was added, the concentration of luciferase contained in each culture supernatant was measured, and luciferase in hypoxia/luciferase in normal condition was determined, based on which the transcription promoting activity in a hypoxic state was studied. The results are shown in FIG. 7.

Example 2

Transfection of Plasmid into Low Oxygen Stimulation Cells and Gene Expression

Utilizing a commercially available GFP expression plasmid (pZsGreen1-1 vector, manufactured by Clontech), a construct inducing GFP by ADAMTS-1 promoter was produced.

Then, the plasmid was transferred (1000 V, 30 msec 2 pulse stimulation) into HUVEC ($2\times10^5$/24 well) by an electroporation method (Microporator: MP-100, manufactured by NanoEnTek Inc. Korea) and, 24 hr later, cobalt chloride (100 μm) chemically mimicking hypoxic state was added and the cells were cultured for 24 hr. Then, the GFP expressing cells were observed by a confocal microscope at excitation wavelength of 488 nm. The results are shown in FIG. 8.

Figure 8:
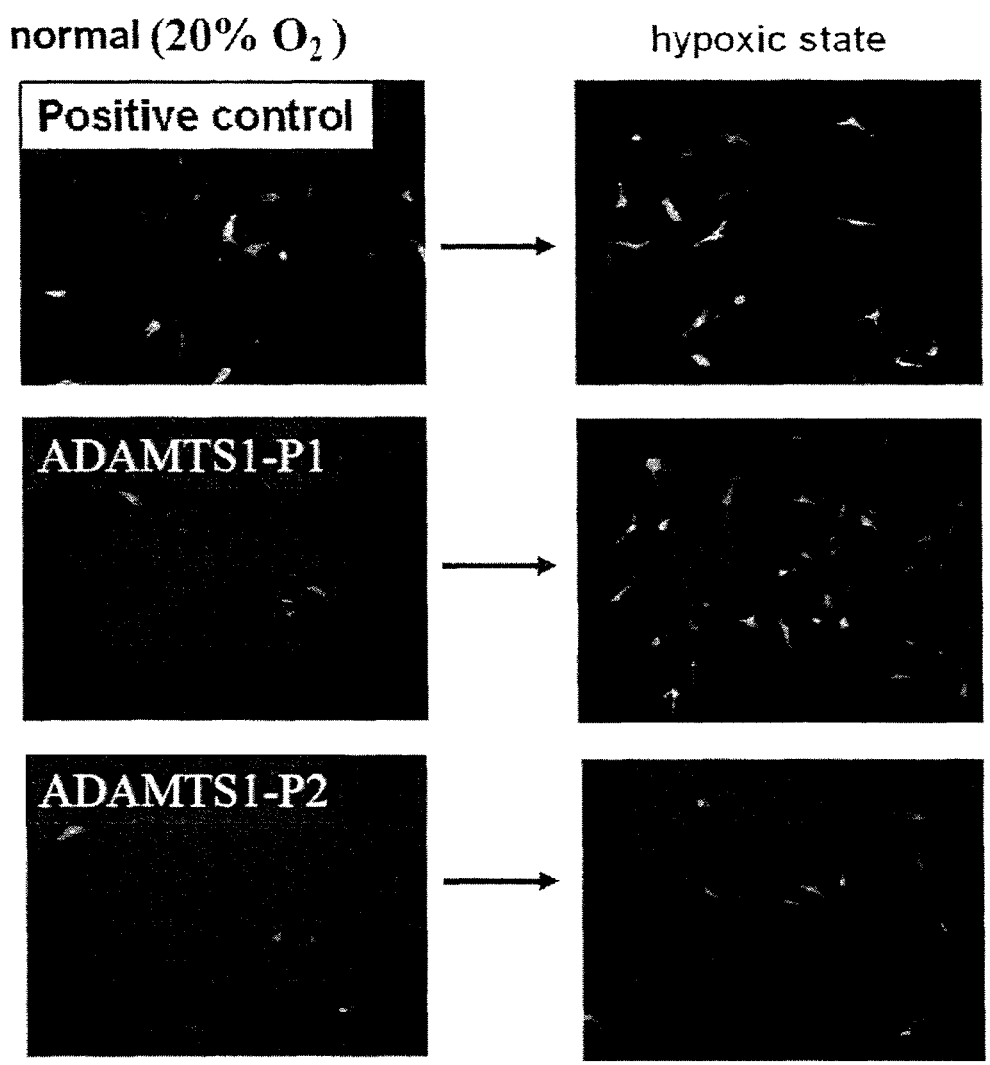
FIG. 8 shows promoter activity of ADAMTS-1 promoter fragments in HUVEC in a low oxygen state. (ADAMTS1-P1 is F3, ADAMTS1-P2 is F6). Hypoxia is at a stage of 24 hr from the addition of cobalt chloride.

In FIG. 8, as a positive control, a vector having GFP connected to the downstream of CMV promoter constitutively expressing in mammalian cells was constructed and transferred into HUVEC in the same manner, and used as the positive control. ADAMTS1-P1 shows application of F3 fragment as a promoter sequence and ADAMTS1-P2 shows application of F6 fragment as the promoter sequence.

INDUSTRIAL APPLICABILITY

The vector of the present invention containing a promoter containing the DNA of the present invention can selectively deliver a medicament of a gene product (protein, RNA) to vascular endothelial cells in a hypoxic state, and therefore, is useful for the prophylaxis and/or treatment of a disease associated with a hypoxic state of vascular endothelial cells, such as acute ischemic disease and the like. In addition, a vector having a reporter gene connected to the downstream of the promoter is useful for an early diagnosis of a disease associated with hypoxia of vascular endothelial cells such as acute ischemic disease and the like. Furthermore, a transgenic non-human animal into which a vector having a reporter gene connected to the downstream of the promoter is useful as an animal material for production of an animal model of a hypoxic state or acute ischemic disease.

This application is based on patent application No. 2008-024071 filed in Japan, the contents of which are encompassed in full in the present specification.

The invention claimed is:

1. A method for promoting vascular endothelial cell-specific transcription of a gene in cells in an acute ischemic stage in a patient, which comprises administrating to the patient by catheter or injection an expression vector comprising a gene operably linked to a promoter such that an effective amount of the expression vector is delivered to the cells in an acute ischemic stage, wherein the promoter comprises a nucleotide sequence having a sequence identity of not less than 80% to (a) the nucleotide sequence of SEQ ID NO: 1 or (b) the nucleotide sequence of a non-human mammalian ortholog of the nucleotide sequence of SEQ ID NO: 1, wherein the non-human mammalian ortholog is a mouse or rat ortholog, and wherein the gene operably linked to the promoter is transiently expressed in the cells in an acute ischemic stage in the patient in a vascular endothelial cell-specific manner, thereby promoting vascular endothelial cell-specific transcription of the gene in the cells in an acute ischemic stage in the patient.

2. The method of claim 1, wherein the promoter comprises a nucleotide sequence having a sequence identity of not less than 90% to (a) the nucleotide sequence of SEQ ID NO: 1 or (b) the nucleotide sequence of a non-human mammalian ortholog of the nucleotide sequence of SEQ ID NO: 1, wherein the non-human mammalian ortholog is a mouse or rat ortholog.

3. The method of claim 2, wherein the promoter comprises a nucleotide sequence having a sequence identity of not less than 95% to (a) the nucleotide sequence of SEQ ID NO: 1 or (b) the nucleotide sequence of a non-human mammalian ortholog of the nucleotide sequence of SEQ ID NO: 1, wherein the non-human mammalian ortholog is a mouse or rat ortholog.

4. The method of claim 1, wherein the gene is selected from the group consisting of vascular endothelial growth factor (VEGF), erythropoietin, hepatocyte growth factor (HGF), basic fibroblast growth factor (FGF), endothelial-derived nitric oxide synthase (eNOS), integrin-linked kinase, B-cell lymphoma (Bcl)-2, Bcl-xL, Bclw, and myeloid cell leukemia (Mcl)-1.

5. The method of claim 1, wherein the expression vector is administered to the patient by catheter.

6. The method of claim 1, wherein the expression vector is administered to the patient by injection.

7. The method of claim 1, wherein the promoter comprises the nucleotide sequence of SEQ ID NO: 1.

8. The method of claim 7, wherein the expression vector is administered to the patient by catheter.

9. The method of claim 7, wherein the expression vector is administered to the patient by injection.

10. The method of claim 1, wherein the promoter comprises the nucleotide sequence of a non-human mammalian ortholog of the nucleotide sequence of SEQ ID NO: 1, wherein the non-human mammalian ortholog is a mouse or rat ortholog.

11. The method of claim 10, wherein the expression vector is administered to the patient by catheter.

12. The method of claim 10, wherein the expression vector is administered to the patient by injection.

13. A method for promoting vascular endothelial cell-specific transcription of a gene in cells in an acute ischemic stage in a patient, which comprises administering an expression vector comprising a gene operably linked to a promoter directly to the cells in an acute ischemic stage in the patient, wherein the promoter comprises a nucleotide sequence having a sequence identity of not less than 80% to (a) the nucleotide sequence of SEQ ID NO: 1 or (b) the nucleotide sequence of a non-human mammalian ortholog of the nucleotide sequence of SEQ ID NO: 1, wherein the non-human mammalian ortholog is a mouse or rat ortholog, and wherein the gene operably linked to the promoter is transiently expressed in the cells in an acute ischemic stage in the patient in a vascular endothelial cell-specific manner, thereby promoting vascular endothelial cell-specific transcription of the gene in the cells in an acute ischemic stage in the patient.

14. The method of claim 13, wherein the promoter comprises a nucleotide sequence having a sequence identity of not less than 90% to (a) the nucleotide sequence of SEQ ID NO: 1 or (b) the nucleotide sequence of a non-human mammalian ortholog of the nucleotide sequence of SEQ ID NO: 1, wherein the non-human mammalian ortholog is a mouse or rat ortholog.

15. The method of claim 14, wherein the promoter comprises a nucleotide sequence having a sequence identity of not less than 95% to (a) the nucleotide sequence of SEQ ID NO: 1 or (b) the nucleotide sequence of a non-human mammalian ortholog of the nucleotide sequence of SEQ ID NO: 1, wherein the non-human mammalian ortholog is a mouse or rat ortholog.

16. The method of claim 13, wherein the promoter comprises the nucleotide sequence of SEQ ID NO: 1.

17. The method of claim 13, wherein the promoter comprises the nucleotide sequence of a non-human mammalian ortholog of the nucleotide sequence of SEQ ID NO: 1, wherein the non-human mammalian ortholog is a mouse or rat ortholog.

* * * * *

SEQUENCE LISTING

```
<160> NUMBER OF SEQ ID NOS: 5

<210> SEQ ID NO 1
<211> LENGTH: 2039
<212> TYPE: DNA
<213> ORGANISM: Homo sapiens
<220> FEATURE:
<221> NAME/KEY: promoter
<222> LOCATION: (1)..(2039)

<400> SEQUENCE: 1
actaagccct tcagaagtaa gctgagttgc ttctctctgc cattcttgct catttgattt      60
ttcctgatga gtggaaagca atgttttgt ttttgttttt caagtaagca atctcgctag     120
gaaaaaagaa gttggaaagc atccggaaaa gaaagcttgt aagagggacg tgtgggagaa     180
ctagaaggga cgcttctggc tggggccaac tgaagtgggg aagatctggg gaggagcgag     240
gaaaggaccc agatctactt ggagccaacc aagagaccgg acgggagtgg ggcggaaagg     300
cggagaccag ttcgagcact aacgcggggg cgcgcgagtg tgagggttgc gggtccgccc     360
ggggctaggg cggtcgctct cgccattgtc cccgcggctt tccgcctgtg aaacacgtcc     420
ttcctctggg tccttgagcc cctcccactt tttggagaga agagccactc agtttttttt     480
cctaaggacc tgttggtgga cctctcctcg ctttcgtaac gcggatatag ccttttccct     540
tcctggtagg aagaggaagg aggggtccgg gaaggaagcc gatttccttc tttcccctc      600 tgcacgcttg ctagcccag cgatcgctgc tggcccccgg gtaggaaagt ggggttcctg      660
gccgtttctg cgacgctggc ctagggcttg cagctgctgt tgagtgaaag cacgcagact     720
ggcgggagcc gatcatttct cgaatgaaga agaaaaagcg caattccctc cttatgctct     780
```

```
agggaattga gccgcgtccc agatcaccca ttccagaaat gtgaaaccgg gccctcacaa    840
agtcgtctct ggtgaagagg tggcgtgcgg ggtgggggtt ggtggagggt gaaggcataa    900
gcaaacatat tttaaaatcc agatcgtagg aagtgtcacc tggcccctca cccaggcatg    960 cttctgggg aagcgcagg gccaagcttt ccctagaaaa gctggggcga agagagagca    1020

(NOTE: reproduction — see image)
```

<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
cactctgcgg aactttttgc                                                19

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
ctccggtggc ttagtggtgt                                                20

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
gcatcatcat gtggcatgtt a                                              21

```
<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
tgtttttccg ttattgtctg                                              20
```